(12) United States Patent
Zemmouri et al.

(10) Patent No.: US 7,794,453 B2
(45) Date of Patent: Sep. 14, 2010

(54) APPARATUS FOR TREATING AGE-RELATED MACULOPATHY (ARM)

(75) Inventors: Jaouad Zemmouri, Hem (FR); Igor Razdobreev, Faches Thumesnil (FR); Andrey Kurkov, Moscow (RU)

(73) Assignee: Universite des Sciences Et Technologies de Lille, Villeneuve d'Ascq Cedex (FR)

( * ) Notice: Subject to any disclaimer, the term of this patent is extended or adjusted under 35 U.S.C. 154(b) by 0 days.

(21) Appl. No.: 10/521,164

(22) PCT Filed: Jul. 17, 2003

(86) PCT No.: PCT/FR03/02259

§ 371 (c)(1),
(2), (4) Date: Jan. 19, 2006

(87) PCT Pub. No.: WO2004/009005

PCT Pub. Date: Jan. 29, 2004

(65) Prior Publication Data
US 2006/0106438 A1 May 18, 2006

(30) Foreign Application Priority Data
Jul. 18, 2002 (FR) .................... 02 09132

(51) Int. Cl.
*A61B 18/18* (2006.01)
(52) U.S. Cl. .................. 606/4; 606/6; 607/89; 128/898

(58) Field of Classification Search ............. 607/88–94; 606/3, 4–6, 7, 16; 128/898
See application file for complete search history.

(56) References Cited

U.S. PATENT DOCUMENTS

| | | | |
|---|---|---|---|
| 5,226,903 A | 7/1993 | Mizuno | |
| 5,873,831 A | 2/1999 | Bernstein et al. | |
| 6,162,242 A | 12/2000 | Peyman | |
| 6,200,309 B1 * | 3/2001 | Rice et al. | 606/10 |
| 6,258,082 B1 * | 7/2001 | Lin | 606/5 |
| 2002/0173832 A1 * | 11/2002 | Strong | 607/88 |
| 2002/0198517 A1 * | 12/2002 | Alfano et al. | 606/8 |
| 2003/0093065 A1 * | 5/2003 | Peyman | 606/4 |
| 2003/0105456 A1 * | 6/2003 | Lin | 606/5 |
| 2003/0120325 A1 | 6/2003 | Fujisaka et al. | |
| 2004/0162549 A1 * | 8/2004 | Altshuler | 606/9 |

FOREIGN PATENT DOCUMENTS

| | | |
|---|---|---|
| WO | WO 9840006 | 9/1998 |
| WO | WO 0183030 | 11/2001 |
| WO | WO 0245633 | 6/2002 |

* cited by examiner

*Primary Examiner*—Henry M Johnson, III
*Assistant Examiner*—Lynsey Crandall
(74) *Attorney, Agent, or Firm*—Millen, White, Zelano & Branigan, P.C.

(57) ABSTRACT

Apparatus for treating age-related macular degeneration, the apparatus comprising a light source which, in operation, serves to emit a therapeutic light beam presenting an emission wavelength lying in the range 1.2 μm to 1.3 μm, and preferably equal to 1.26 μm to 1.27 μm. The laser source is preferably comprises an optical fiber Raman laser.

4 Claims, 2 Drawing Sheets

APPARATUS FOR TREATING AGE-RELATED MACULOPATHY (ARM)

The present invention relates to an apparatus used in ophthalmology for treating age-related macular degeneration (ARMD), and more particularly ARMD of the exudative type, by means of a light beam, and more particularly by means of a "non-thermal" laser.

BACKGROUND OF THE INVENTION

Age-related macular degeneration (ARMD) constitutes a severe threat to vision, and the frequency of cases of ARMD is tending to increase because of lengthening lifetimes and various environmental factors and daily exposure to light, which factors are also combined with genetic predispositions.

ARMD results in a progressive loss of macular vision cells as described hereinafter. It is the major cause of poor vision in industrialized countries for people aged more than fifty, but it affects the macula only. It therefore cannot lead to complete blindness.

There are two main forms of ARMD:

Dry or atrophic ARMD which is characterized by the formation of small spots or "drusen" under the retina and by atrophy of the retinal pigmentary epithelium. There exists no treatment for this type of ARMD, in particular by means of a laser.

Wet or exudative ARMD is characterized by the presence of abnormal blood vessels or neovascularization. These vessels are fragile, can bleed, leak, develop, and progressively destroy the macula. As a general rule, in order to be able to see them, it is necessary to perform angiography which displays them accurately. Angiography using fluorescein reveals fluid leaks and retinal neovascularization, while angiography using indocyanine green reveals choroidal and occult new vessels. Angiography consists in injecting dye into the veins in order to observe retinal and choroidal blood vessels effectiveness on a clinical form of new vessels, i.e., vessels visible neovascularization outside or beside the fovea.

The first signs of the disease can be seen only by an ophthalmologist, and they are detected by examining the back of the eye, and possibly also by performing angiography with fluorescein or indocyanine green. The patient perceives symptoms only once the disease has already reached an advanced stage. There is no pain.

The most common symptom is a loss of visual acuity: initially in the form of a need for increased light levels when reading. Fewer details can be seen and certain features of the face disappear or certain letters or words in a phrase disappear when reading. Another symptom is alarming and makes people consult quickly: this is the appearance of straight lines that become deformed.

At a more advanced stage, central vision is highly degraded (a black spot in the center of the field of vision): faces are no longer recognized, and reading and writing become impossible. Peripheral vision is conserved and allows the patient to be mobile and remain independent.

Various treatments are made available to patients suffering from ARMD. Therapeutic indications cannot be described in greater detail insofar as numerous treatments are presently under evaluation. In addition, none of those treatments enables ARMD to be cured. It is possible only to halt degeneration or to slow down the advance of the disease.

There are thermal-type treatments in which a heating effect is looked-for and used, and there are other treatments.

The two thermal-type treatments are photocoagulation by laser treatment and thermal therapy through the pupil.

Photocoagulation by Laser Treatment

This is the first treatment to have demonstrated effectiveness on a clinical form of new vessels; visible neovascularization outside or beside the fovea.

This treatment is difficult to perform. The purpose of the treatment is to burn the new vessels by releasing a high temperature in the vicinity thereof. More precisely, the coherent laser beam interacts with the back portion of the retina (the pigmentary epithelium) which absorbs light. This reaction raises the temperature at the back of the epithelium, thereby also leading in harmful manner to definitive lesions in the photodetectors.

Transpupillary Thermal Therapy (TTT)

Transpupillary thermal therapy is treatment that consists in using a laser to heat the zone for treatment as in laser photocoagulation treatment. However, in this treatment, the laser beam is used to raise temperature to a smaller extent than with conventional photocoagulation treatment. This is in an attempt to avoid the above-mentioned lesions due to using a laser that gives off high temperatures. Nevertheless, in order to obtain a therapeutic effect while heating less strongly, it is necessary to apply the laser beam for a longer duration (several tens of seconds). This is described in international patent application WO 02/45633. In particular, the recommended duration of irradiation for this treatment lies in the range 30 seconds (s) to 40 s. Unfortunately, any laser treatment is precision treatment that requires the zone for treatment to remain stationary throughout the duration of the treatment. Keeping a patient's eye stationary for several tens of seconds is not possible, unless the treatment is applied under anesthesia.

There are also two non-thermal type treatments using conventional medication and dynamic phototherapy.

Medication Treatments

At present, no treatment by medication has been successful. The treatments that have been studied the most are those relying on supplying additional oligo-elements and vitamins: vitamins A and E, selenium, zinc, . . . . The idea is to cause the retina to operate under better metabolic conditions and thus limit the risk of accumulating the waste associated with aging.

Dynamic Phototherapy (DPT)

Dynamic phototherapy is a recent method which consists in combining a photosensitive drug with a "non-thermal" laser (one that does not burn the retina), in contrast to the lasers used for photocoagulation.

A photosensitive drug, such as Verteporfin sold under the trademark VISUDYNE®, for example, is injected intravenously into the body of the patient. This drug rapidly reaches the abnormal blood vessels of the retina where it becomes fixed to the inside walls of these new vessels. Thereafter, the portion of the macula that is to be treated is illuminated with a red laser, e.g. at a wavelength of 689 nanometers (nm), and for a duration of 90 s. The laser beam serves to activate the photosensitive drug which leads to a sequence of chemical reactions taking place inside the new vessels, causing the abnormal vessels in the retina to become occluded, and subsequently to disappear. More particularly, the action of the laser beam on the molecules of the photosensitive substance serves mainly to generate singlet oxygen ($^1O_2$), which is the main agent serving to occlude abnormal retinal vessels.

The latest studies have given results that are very satisfactory, with 60% of patients treated presenting visual acuity that is stabilized or improved. Nevertheless, that method presents several drawbacks. The first drawback is associated with patients being photosensitized, which obliges them to avoid any exposure to the sun for a relatively long period of time, generally of the order of 48 hours (h). Another drawback is associated with injecting a drug (a photosensitive substance) that is expensive, thus making the treatment expensive, it being understood that the treatment needs to be repeated in order to be effective. Finally, with some patients, injecting a photosensitive drug can lead to side effects that are harmful.

OBJECTS AND SUMMARY OF THE INVENTION

An object of the present invention is thus to provide a method and apparatus for treating ARMD, and in particular wet ARMD, which, in a manner comparable with dynamic phototherapy, make use of a therapeutic light beam that is non-thermal and non-destructive (unlike the laser used for photocoagulation or in transpupillary thermal therapy), but which do not require a photosensitive drug to be injected.

The technique of the invention relies on using a laser source that presents an emission wavelength lying in the range 1.2 micrometers (μm) to 1.3 μm, and preferably in the range 1.26 μm to 1.27 μm.

The invention thus provides apparatus for laser treatment of age-related macular degeneration, which apparatus includes, in known manner, a light source that, in operation, serves to emit a non-thermal therapeutic light beam.

In a manner characteristic of the invention, said light source is designed to emit a non-thermal therapeutic light beam presenting an emission wavelength lying in the range 1.2 μm to 1.3 μm, and preferably in the range 1.26 μm to 1.27 μm, so as to lie in the wavelength range that corresponds specifically to the molecular transition of oxygen, thus enabling intracellular singlet oxygen to be generated directly and in sufficient quantity.

The invention also provides a method of treating age-related macular degeneration consisting in illuminating the macula with a non-thermal therapeutic light beam presenting an emission wavelength lying in the range 1.2 μm to 1.3 μm, and preferably in the range 1.26 μm to 1.27 μm, so as to lie in a wavelength range corresponding specifically to the molecular transition of oxygen, thus enabling intracellular singlet oxygen to be generated directly and in sufficient quantity.

The light source is preferably a laser source producing a coherent therapeutic light beam.

Preferably, but in a manner that is not limiting for the invention, the laser source used is an optical fiber Raman laser.

More particularly, the power of the laser source lies in the range 1 milliwatt (mW) to 1 watt (W), and preferably lies in the range 10 mW to 1 W.

It has been found that using a therapeutic light beam at the above-specified particular frequencies makes it possible advantageously and in surprising manner to obtain results that are satisfactory when treating ARMD (retarding the loss of visual acuity, and possibly even improving visual acuity), without it being necessary to use a drug. A posteriori, it seems plausible that the action of the therapeutic light beam in the above-specified wavelength range serves to generate singlet oxygen directly from the blood contained in the new vessels, and does so in sufficient quantity to obtain therapeutic effects that are comparable to those obtained after injecting a photosensitive drug. Thus, unlike the above-mentioned DPT method, the light beam no longer acts on an intermediate substance (the photosensitive drug) in order to generate singlet oxygen, but given the above-mentioned particular wavelength range of the light beam used in the invention, said beam acts directly on the oxygen contained in the new vessels in order to generate singlet oxygen. Nevertheless, the Applicant is not tied to this explanation.

BRIEF DESCRIPTION OF THE DRAWINGS

Other characteristics and advantages of the invention appear more clearly in the light of the following description of a preferred embodiment of treatment apparatus of the invention and of its method of use, which description is given by way of non-limiting example and with reference to the accompanying drawings, in which.

MORE DETAILED DESCRIPTION

Figure 1:
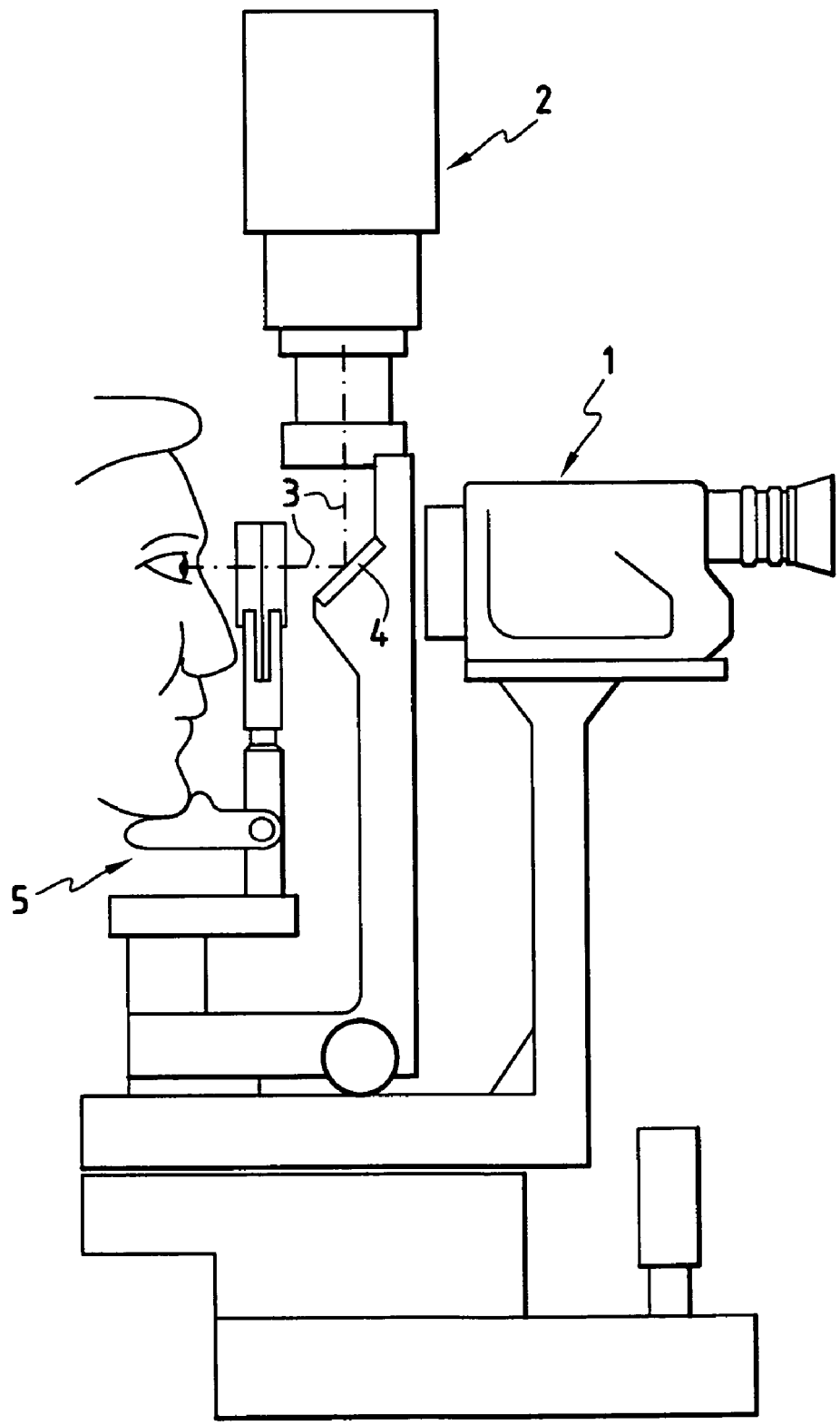
FIG. 1 shows an example of treatment apparatus of the invention of the type having a slit-lamp.

FIG. 1 shows an embodiment of apparatus of the invention for treating ARMD, which apparatus is of the slit-lamp type.

In the usual manner for slit-lamps, this apparatus essentially comprises:

an optical unit 1 enabling a practitioner to observe the eye being treated;

a treatment unit 2 serving to generate a light beam 3, which beam is directed vertically on leaving the treatment unit 2, in the present example;

a mirror 4 for deflecting the light beam 3 through 90° so that it propagates horizontally on the same optical axis as the optical observation axis of the optical unit 2; and means 5 of the chin-rest type for positioning the patient's head relative to the optical unit 1 and the light beam 3, and thus positioning the eye that is to be treated.

Figure 2:
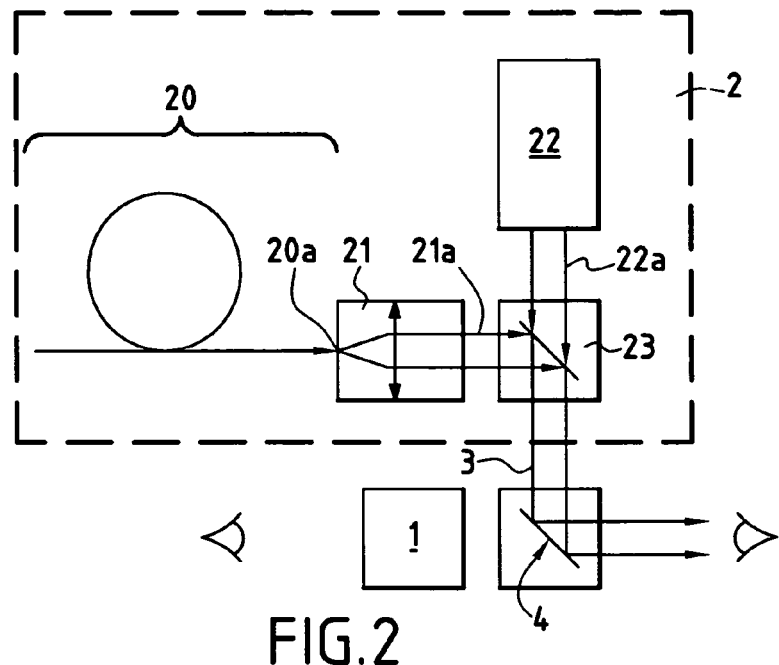
FIG. 2 is a diagram showing the two main light sources (the therapeutic source and the illumination source) mounted inside the treatment unit of the FIG. 1 apparatus.

With reference to FIG. 2, the treatment unit 2 comprises a therapeutic light source 20 and a conventional light source 22 for illuminating the eye (standard illumination lamp). The therapeutic light beam 20a coming from the source 20 is coupled in conventional manner with the illuminating beam 22a coming from the light source 22 by means of an optical coupling system 23, after being shaped in conventional manner (using an optical collimator system 21). In operation, the above-mentioned light beam 3 is emitted from the outlet of the treatment unit 2, which beam corresponds both to the therapeutic light beam and to a non-therapeutic light beam enabling the eye to be illuminated so that the eye can be observed by means of the optical unit 1.

The invention lies in the light source 20 of the unit 2, which light source is described in greater detail below. The other elements of the apparatus are those that are usually implemented in prior art slit-lamps, so they are not described in greater detail below.

In the general manner of the invention, the light source 20 is designed to emit a therapeutic light beam 20a presenting an emission wavelength lying in the range 1.2 μm to 1.3 μm.

The therapeutic light beam 20a is preferably a coherent light beam (laser). Nevertheless, in another embodiment, the therapeutic light beam 20a could be a non-coherent light beam generated by a light source of sufficient power followed by optical filtering so as to retain only those frequency components that lie in the range 1.2 μm to 1.3 μm.

When the beam 20a comprises coherent light, the most general definition of the invention is not limited to any particular type of laser source 20, and any laser source that is suitable for emitting a laser beam satisfying the above-specified wavelength condition and known to the person skilled in the art could be used. In particular, and in non-exhaustive manner, it is possible to use laser sources of the following types:
- a continuous or pulsed optical fiber Raman laser;
- a continuous or pulsed Cr: Forsterite ($Cr_4+$: $Mg_2SiO_4$) laser optically pumped by a neodymium-doped (Nd-doped) optical fiber or solid laser, by an ytterbium-doped (Yb-doped) optical fiber or solid laser, or by a diode;
- a continuous or pulsed parametric oscillator, pumped by another laser source;
- a laser diode; or
- a continuous or pulsed solid Raman converter or laser pumped by another laser source.

Amongst the above lasers, it is preferable to use an optical fiber Raman laser, mainly for the following reasons:
- the fiber outlet from the laser makes it easier to convey the beam to the outlet of the treatment unit 2;
- the laser beam 20a that is generated thereby presents good spatial and spectral quality;
- in advantageous manner, the laser source 20 is compact;
- the laser source 20 is reliable and does not require any maintenance; and
- this type of laser source provides the best compromise between quality and manufacturing cost of the laser.

Figure 3:
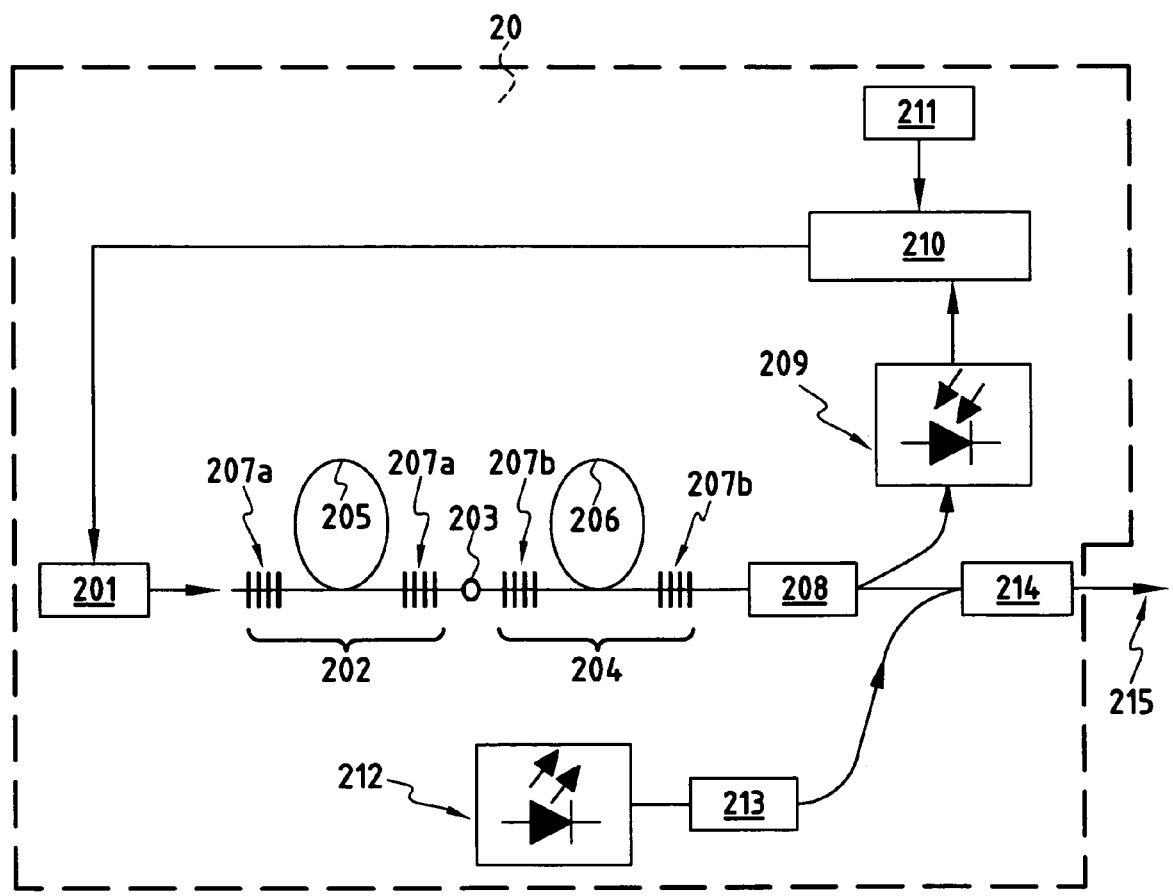
FIG. 3 is a diagram of an optical fiber Raman laser implemented in the FIG. 1 apparatus.

Preferred Embodiment of an Optical Fiber Raman Laser having a Wavelength Lying in the Range 1.2 μm to 1.3 μm (FIG. 3)

The laser source 20 used in the treatment unit 2 is preferably an optical fiber Raman laser designed to emit a therapeutic laser beam 20a at a wavelength in the range 1.26 μm to 1.27 μm, and at a power level lying in the range 1 mW to 1 W, and preferably in the range 10 mW to 1 W.

With reference to FIG. 3, the optical fiber Raman laser comprises a pumped laser diode 201 at a wavelength of 910 nm to 930 nm or 970 nm to 980 nm, an ytterbium-doped optical fiber laser 202, and a Raman converter 204 serving to transpose the wavelength of the beam being output by the optical fiber laser 202 so as to obtain a laser beam having a wavelength in the range 1260 nm to 1270 nm.

The Yb-doped optical fiber laser 202 is constituted by a dual-clad optical fiber 205 with an ytterbium-doped core and two Bragg gratings 207a, one at its inlet and another at its outlet, which gratings are photo-inscribed in the fiber. The outlet 203 of the Yb laser fiber 202 is welded directly to the inlet of the Raman converter 204.

The Raman converter 204 comprises an optical fiber 206 with a phosphorous-doped core and two Bragg gratings 207b, one at its inlet and the other at its outlet, which gratings are adjusted to a wavelength in the range 1260 nm to 1270 nm. This converter serves to transpose the emission wavelength of the Yb laser 202 in a single step.

In another variant, it is possible to use a monomode or a multimode optical fiber different from the fiber described above; under such circumstances, the number of conversion steps performed by the Raman converter 204 needs to be adapted as a function of the nature of the fiber, and in particular of the dopant used.

It is also possible to replace the Bragg gratings by monomode couplers.

Power is controlled by means of a coupler 208 presenting a low coupling ratio, and a photodiode 209 connected to control electronics 210, serving to control the outlet power 215, e.g. by acting directly on the current fed to the pump diode 201. The control electronics 210 enables the practitioner to adjust the power of the therapeutic laser beam 20a manually over the range 1 mW to 1 W, and preferably over the range 10 mW to 1 W.

By way of example, the outlet 215 of the optical fiber Raman laser is fitted with an outlet connector (not shown in the figures, but constituted by an FC, SMA, etc. type connector) serving to enable it to be connected easily and directly to the collimator optical system 21 of the slit-lamp.

An actuation pedal 211 or equivalent means connected to the control electronics 210 is also provided to enable the practitioner to control triggering of the therapeutic laser beam 20a.

According to an additional characteristic, the laser source 20 also includes aiming means 212, 213, and 214. More particularly, these aiming means comprise a red optical fiber laser diode 212 which emits in the wavelength range 630 nm to 690 nm and which is coupled to the outlet of the optical fiber Raman laser via an attenuator 213 and a monomode wavelength-division multiplex (WDM) coupler 214. The diode 212 serves as an aiming source and enables the practitioner (via the optical unit 1) to view the point of impact of the therapeutic laser beam.

The optical fiber Raman laser described above with reference to FIG. 3 and serving to emit a therapeutic laser beam at a wavelength lying in the range 1.2 μm to 1.3 μm is novel in itself, and can thus advantageously also be used in other applications, whether medical or non medical, and outside the particular field of treating ARMD.

The apparatus of the invention is implemented as follows. The patient places his/her head on the chin rest 5. The practitioner adjusts the three-dimensional position of the eye that is to be treated relative to the beam 3 in very accurate, but conventional, manner by visualizing the impact of the therapeutic laser beam 20a by means of the aiming beam that is produced continuously by the diode 212. Once alignment is exact, the practitioner adjusts the emission power of the therapeutic laser 20a and actuates the control pedal or equivalent 211 for a predetermined length of time, thereby causing the therapeutic laser beam to be emitted (to illuminate the zone of the macula that is to be treated). The duration of the treatment is determined by the practitioner. Electronic means for controlling this treatment duration may optionally be provided in the apparatus. Once the target zone of the macula has been treated, the practitioner repeats the same operations on a new diseased zone (the eye being newly aligned relative to the beam 3).

What is claimed is:

1. A method of treating age-related macular degeneration without using an external photosensitizer, the method comprising selecting a laser light source that enables a non-thermal therapeutic laser light beam to be emitted in a manner similar to laser light sources used for dynamic therapy, said light source being designed to emit a therapeutic laser light beam, presenting an emission wavelength lying in the range 1.26 μm to 1.27 μm at a power in the range of 1 mW to 1 W and illuminating the macula of the patient with said laser light beam to generate in the retina intracellular singlet oxygen directly and in sufficient quantity to occlude abnormal retinal vessels.

2. The method according to claim 1, wherein the power of the therapeutic light beam is in the range of 10 mW to 1 W.

3. A method according to claim 1, wherein the laser light source comprises an optical fiber Raman laser.

4. A method according to claim 3, wherein the optical fiber Raman laser comprises a pump laser diode, an ytterbium-doped optical fiber laser, and a Raman converter serving to transpose the wavelength of the beam coming from the ytterbium-doped optical fiber laser.

* * * * *